United States Patent
Wilkinson

Patent Number: 6,053,946
Date of Patent: Apr. 25, 2000

[54] FLEXIBLE PROSTHETIC FOOT APPARATUS

[76] Inventor: Kerry E. Wilkinson, 5750 W. Linda La., Chandler, Ariz. 85226

[21] Appl. No.: 09/028,199

[22] Filed: Feb. 23, 1998

[51] Int. Cl.⁷ ........................................................ A61F 2/66
[52] U.S. Cl. ................................................ 623/52; 623/55
[58] Field of Search .................. 623/47, 50, 52, 623/53, 55, 56

[56] References Cited

U.S. PATENT DOCUMENTS

| | | | |
|---|---|---|---|
| 61,780 | 2/1867 | Watson | 623/33 |
| 831,330 | 9/1906 | Doebrich | 623/53 X |
| 4,547,913 | 10/1985 | Phillips . | |
| 4,645,509 | 2/1987 | Poggi et al. | 623/55 |
| 4,822,363 | 4/1989 | Phillips | 623/27 |
| 4,938,776 | 7/1990 | Masinter | 623/49 |
| 4,959,073 | 9/1990 | Merlette | 623/55 |
| 5,062,859 | 11/1991 | Naeder . | |
| 5,156,631 | 10/1992 | Merlette . | |
| 5,219,364 | 6/1993 | Lloyd | 623/33 |
| 5,258,039 | 11/1993 | Goh . | |
| 5,376,140 | 12/1994 | Ryan . | |
| 5,486,209 | 1/1996 | Phillips . | |
| 5,507,838 | 4/1996 | Chen . | |
| 5,549,714 | 8/1996 | Phillips . | |
| 5,593,456 | 1/1997 | Merlette . | |
| 5,593,457 | 1/1997 | Phillips . | |

*Primary Examiner*—David H. Willse
*Attorney, Agent, or Firm*—H. Gordon Shields

[57] ABSTRACT

Prosthetic foot apparatus includes a tubular element appropriately bent and flattened to provide desired flexibility. The extent of flexibility, and accordingly the extent of the bending and flattening of the tubular element provides desired stiffness or flexibility according to the desired characteristic, complementary of the user of the apparatus. Different embodiments are shown, including an embodiment which includes a separate foot plate secured to and extending into the foot portion of the tubular element.

5 Claims, 1 Drawing Sheet

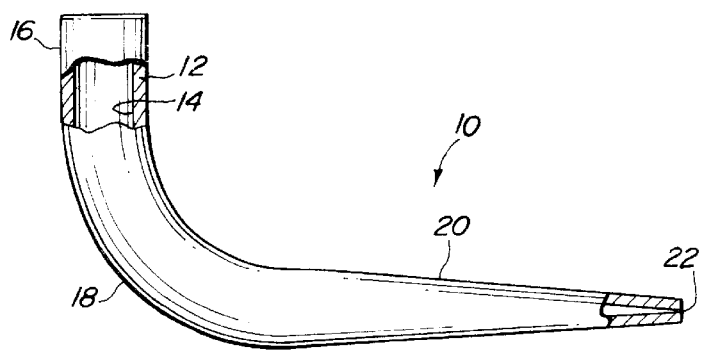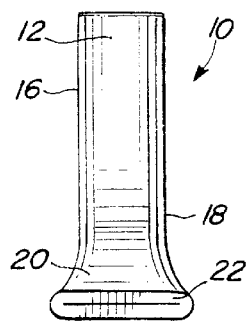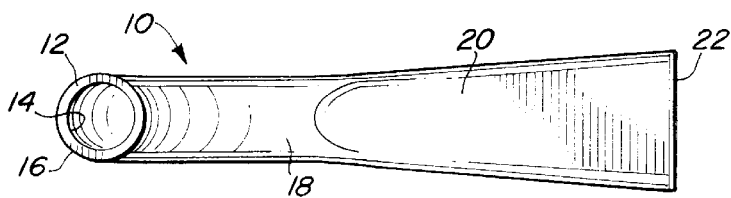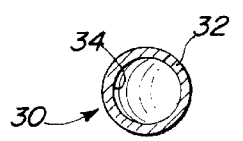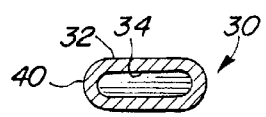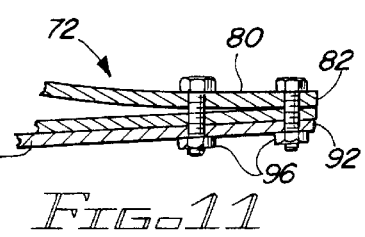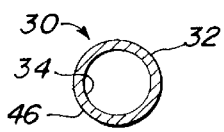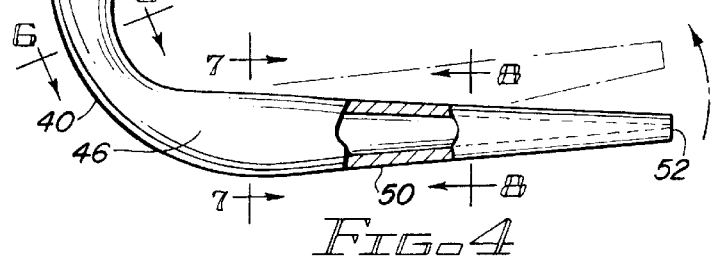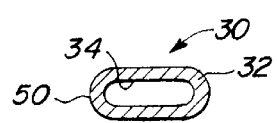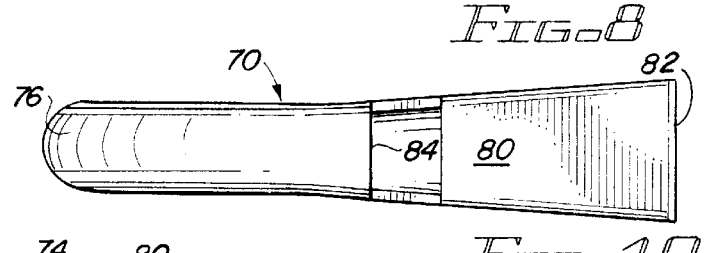

FLEXIBLE PROSTHETIC FOOT APPARATUS

BACKGROUND OF THE INVENTION

1. Field of the Invention

This invention relates to prosthetic appliances and, more particularly, to a flexible prosthetic foot.

2. Description of the Prior Art

U.S. Pat. No. 4,547,913 (Phillips) relates to a composite prosthetic foot and leg which includes three portions, a leg portion, a foot portion, and a heel portion. The three portions are joined together rigidly. The three elements provide a degree of flexibility in response to ankle movements and foot movements, but provide sidewise rigidity. Various embodiments are disclosed.

U.S. Pat. No. 4,822,363 (Phillips) provides a different embodiment by the same inventor as the '913 patent, discussed above. The apparatus is made of laminated material to provide a prosthetic leg connected to a prosthetic foot. The leg portion is curved to define the foot, with a separate head portion connected to the foot portion. Various stiffness may be provided in the foot portion. Again different embodiments are disclosed.

U.S. Pat. No. 5,062,859 (Naeder) discloses a prosthetic foot which includes a resilient foot insert. The foot insert is of a general "Z" configuration. Different embodiments are illustrated.

U.S. Pat. No. 5,156,631 (Merlette) discloses a prosthetic foot and leg in which a leg element curves to define a foot element, and a separate segment is bonded to the forward extending foot portion extension of the leg element. The separate foot portion comprises or defines a sole element.

U.S. Pat. No. 5,258,039 (Goh et al) discloses a prosthetic foot apparatus made of resin impregnated woven fabric material. The apparatus is made of two segments both of which are curved to define a foot and heel portion and which provides the substantial degree of flexibility. Various embodiments or configurations are disclosed.

U.S. Pat. No. 5,376,140 (Ryan) discloses a prosthetic foot apparatus made of composite material. The apparatus has a general configuration of a natural foot with various elements involved, including a foamed polymer body, and cushioning material provides elasticity and flexion.

U.S. Pat. No. 5,486,209 (Phillips) discloses a prosthetic foot apparatus made of laminated materials. The apparatus includes an ankle portion, a foot portion, and a heel portion. Various configurations are illustrated.

U.S. Pat. No. 5,507,838 (Chen) discloses an artificial foot apparatus having a foot shaped casing and insert elements into the casing.

U.S. Pat. No. 5,549,714 (Phillips) discloses another prosthetic foot apparatus made of different elements secured together. Various elements are interchangeable to match the weight, stride, and activity schedule of the user of the apparatus.

U.S. Pat. No. 5,593,456 (Merlette) discloses another prosthetic leg and foot apparatus made of a single monolithic elongated composite member. The member includes a semi-flexible shank portion, an ankle portion, a fore-foot portion, and a toe portion. The apparatus is designed primarily for athletic type use.

U.S. Pat. No. 5,593,457 (Phillips) discloses apparatus similar to that disclosed in the above referred '290 patent. Both the '290 patent and the '457 patent are continuations of the same parent application.

SUMMARY OF THE INVENTION

The invention claims and described herein comprises a prosthetic foot made of a single tubular element which is flattened or configured to provide the degree of flexibility for the element. A second embodiment includes a flat plate appropriately secured to and extending inside of a foot portion of the tubular element.

Among the objects of the present invention are the following:

To provide new and useful prosthetic foot apparatus;

To provide new and useful prosthetic foot apparatus including a tubular element;

To provide new and useful prosthetic foot apparatus made of a tubular element and appropriately flattened or configured to provide a desired degree of flexibility;

To provide new and useful prosthetic foot apparatus including a flat plate secured to a tubular element; and To provide new and useful prosthetic foot apparatus having a flat plate element secured to and extending into the interior of a foot portion of a tubular element.

BRIEF DESCRIPTION OF THE DRAWING

FIG. 1 is a side view in partial section of the apparatus of the present invention.

FIG. 2 is a front view of the apparatus of FIG. 1.

FIG. 3 is a top view of the apparatus of FIGS. 1 and 2.

FIG. 4 is a side view of an alternate embodiment of the apparatus of FIGS. 1, 2, and 3.

FIG. 5 is a view in partial section taken generally along line 5—5 of FIG. 4.

FIG. 6 is a view in partial section taken generally along line 6—6 of FIG. 4.

FIG. 7 is a view in partial section taken generally along line 7—7 of FIG. 4.

FIG. 8 is a view in partial section taken generally along line 8—8 of FIG. 4.

FIG. 9 is a view in partial section of an alternate embodiment of the apparatus of the present invention.

FIG. 10 is a view in partial section taken generally along line 10—10 of FIG. 9.

FIG. 11 is a view in partial section of an alternate embodiment of FIGS. 9 and 10.

DESCRIPTION OF THE PREFERRED EMBODIMENT

FIG. 1 is a side view of flexible prosthetic foot apparatus 10 of the present invention. FIG. 2 is a front view of the foot apparatus 10 of FIG. 1. FIG. 3 is a top view of the flexible foot apparatus 10 of FIGS. 1 and 2. For the following discussion, reference will be made to FIGS. 1, 2, and 3.

The flexible foot apparatus 10 comprises a tubular element 12 in which there is a bore 14. The foot apparatus 10 may be divided into three portions, an upper, straight portion 16, a curved, ankle portion 18, and a tapering lower portion 20. The lower portion tapers to a toe end 22 in which the tube 18 is substantially flat. The flattening of the tube 12 in the lower foot portion 20 results in an outward tapering of the lower foot portion 20, outwardly from the curved portion 18 to the end 22. This is best shown in FIG. 3.

In the side view of FIG. 1, the gradual tapering of the tube 12 from the upper straight or full diameter portion 16, through the curved portion 18, onto the foot portion 20, and terminating in the toe end 22 is shown. The degree or extent of flexing varies according to the degree or extent of the flattening of the tube. In the embodiment of FIGS. 1–3, there will be some flexing in the curved portion 18, as an ankle flexing, but even more in the foot portion 20 and in the toe area 22.

FIG. 4 is a side view, partially broken away, of an alternate embodiment 30 of the apparatus 10 in FIGS. 1, 2, and 3. FIG. 5 is a view in partial section of the apparatus 30 taken generally along line 5—5 of FIG. 4. FIG. 6 is a view in partial section taken generally along line 6—6 of FIG. 4, while FIG. 7 is a view in partial section taken generally along line 7—7 of FIG. 4, and FIG. 8 is a view in partial section taken generally along line 8—8 of FIG. 4. For the following discussion, reference will be made to FIGS. 4, 5, 6, 7, and 8.

The flexible foot apparatus 30 is made of a tube 32 which has an interior bore 34. The flexible foot apparatus 30 includes a relatively straight upper portion 36, which corresponds to the upper portion 16 of the apparatus 10. The tubular member 32 includes a bore 34. The tubular member 32 is generally circular, and accordingly the bore 34 is generally circular.

Downwardly from the upper, straight portion 36 is a partially flattened or necked down curved portion 40. The portion 40 corresponds to an ankle portion of a natural leg in that there is flexing to a degree permitted in the area 40 by the flattening or necking down of the tube 32. The general flattening of the tube 32 in the area 40 is illustrated in detail in FIG. 6.

Downwardly from the neck down or flattened portion 40 is another circular or full cross-sectional area 46. In the area 46, the tubular member 30 is at a full diameter cross-sectional configuration, as illustrated in FIG. 7.

From the lower circular portion 46, the tubular member 32 tapers to an outer end 52. The tapering portion 50 is similar to the tapering front foot portion 20 of the apparatus 10. The tapering is accomplished by a gradual flattening of the tube 32 until the tubular member 32 is flattened to terminate at the end 52. The end 52, in an end view, is substantial the same as that illustrated in FIG. 2 for the end 22 of the tubular member 12.

In dash/dot line in FIG. 4, the flexing of the "ankle" portion 40 is illustrated. The dash/dot arrow adjacent to the tip 52 illustrates the relative movement of the foot tapering portion 50 relative to the upper straight portion 36. Again, the flexing is permitted or allowed by the necking down, or semi flattening of the tube 32 in the area 40, as illustrated in FIG. 6.

By varying the cross section of the tubular member 32 in the "ankle" portion 40, the flexing of the apparatus is varied. The greater the extent of the flattening or necking down, the greater the degree of flexing, and vice versa. Thus, in addition to the flexing of the portion 40, there will also be some flexing in the bottom foot portion 50 due to the flattening of the tubular member 32. This latter flexing provides a degree of springiness to the apparatus 30.

FIG. 9 comprises a side view in partial section of an alternate embodiment 70 of the apparatus of the present invention. The apparatus 70 is another alternate embodiment of the apparatus 10 of FIGS. 1, 2, and 3. FIG. 10 is a bottom view taken generally along ling 10—10 of FIG. 9. For the following discussion, reference will be made primarily to FIGS. 9 and 10.

The flexible prosthetic foot apparatus 70 is again made of a tubular member 72 which has a bore 74. The apparatus 70 includes an upper portion 76 which is generally straight, and accordingly the cross-sectional configuration of the tubular member 70 will be circular, such as illustrated in FIGS. 3, 5, and 7, for the apparatus 10 and 30. The straight upper portion 76 then curves to define a portion 76, which may be considered as an ankle portion. From the curved portion 76, the tubular member 72 is tapered inwardly and flattened and terminates in a front end or toe tip 82. The continual tapering of the flattening of the tubular member 72 from the upper straight portion 76 to the toe tip 82 may be understood from FIG. 9.

On the bottom of the tubular member 76, at the tapering foot portion 80, there is a slot 84. The front end of a plate 90 extends through the slot 84 and extends to the tip 82 where the plate terminates in an end 92. An appropriate fastener 94, such as a rivet, may be used to secure the plate 90 to the foot portion 80, if desired or if required. However, as shown in FIG. 9, and as also may be understood from FIG. 2 and from FIGS. 1 and 4, the end or tip 82 of the tubular member 76 is flattened so that the plate 90 is held relatively securely therein. Thus, at the front end of the foot portion 80, the tips 92 of the plate 90 and 82 of the tube 72 are flattened adjacent to each other.

The flattening of the tube 72 in the foot area 80, resulting from the inward taper of the tube 72, results in an outward taper of the portion 80, as best illustrated in FIG. 10.

FIG. 11 is a fragmentary view in partial section of an alternate embodiment of the apparatus 70 from that illustrated in FIG. 9. Instead of having the plate 90 extend through the slot 84 and into the interior bore 74 of the tubular member 72 at the foot portion 80, the plate 92 is simply appropriately secured to the bottom of the foot portion 80 by a pair of appropriate fasteners 96, such as nuts and bolts. This eliminates the need for the slot 84.

Three embodiments of a flexible prosthetic foot are illustrated and have been discussed. They all share in construction in that a tubular member is used to form the vertical portion of the foot and which is appropriately connected to a leg member or other prosthesis, not shown, but as is well known and understood. The tubular member curves to define an ankle portion between the vertical portion and a foot portion. Deformation of the ankle portion provides flexibility to create to a degree the desired movement. Flexing of the tubular member varies according to the flattening or deformation in the cross sectional configuration, as discussed above. The greater the extent of flattening of the tubular member, the greater the degree or extent of the flexibility.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, within the limits only of the true spirit and scope of the invention.

What I claim is:

1. Prosthetic foot apparatus comprising in combination:

a resilient tubular prosthetic support element including
   a relatively straight upper tubular portion,
   a curved middle tubular portion,
   a lower tubular portion terminating in a relatively flattened end; and the curved middle tubular portion is flattened to allow flexing of the tubular element.

2. The apparatus of claim 1 which further includes a plate secured to the lower tubular portion.

3. The apparatus of claim 2 in which the lower tubular portion includes a slot and the plate extends into the slot to secure the plate to the lower tubular portion.

4. The apparatus of claim 1 in which the flattening of the curved middle tubular portion is tapered to the lower tubular portion.

5. The apparatus of claim 4 in which the flattening of the curved middle tubular portion tapers on to the lower tubular portion.

* * * * *